United States Patent [19]

Kutsch et al.

[11] Patent Number: 5,601,430

[45] Date of Patent: Feb. 11, 1997

[54] PROCESS FOR THE REMOVAL OF SOFT TOOTH DECAY USING A UNIQUE ABRASIVE FLUID STREAM

[75] Inventors: V. Kim Kutsch, Albany, Oreg.; Michael Everett, Glendale, Calif.

[73] Assignee: Kreativ, Inc., Albany, Oreg.

[21] Appl. No.: 528,850

[22] Filed: Sep. 15, 1995

[51] Int. Cl.$^6$ ................................................ A61C 15/00
[52] U.S. Cl. ...................................... 433/215; 433/216
[58] Field of Search ................................ 433/82, 88, 215, 433/216; 51/410, 438, 427, 436

[56] References Cited

U.S. PATENT DOCUMENTS

| | | | |
|---|---|---|---|
| 3,344,524 | 10/1967 | Kulischenko | 32/58 |
| 3,852,918 | 12/1974 | Black | 51/12 |
| 3,866,357 | 2/1975 | Callahan et al. | 51/12 |
| 4,214,871 | 7/1980 | Arnold | 433/216 |
| 4,494,932 | 1/1985 | Rzewinski | 433/88 |
| 4,635,897 | 1/1987 | Gallant | 251/5 |
| 4,663,153 | 5/1987 | Winston et al. | 424/52 |
| 4,696,645 | 9/1987 | Saupe et al. | 433/88 X |
| 4,708,534 | 11/1987 | Gallant | 406/75 |
| 4,731,125 | 3/1988 | Carr | 134/51 |
| 4,733,503 | 3/1988 | Gallant et al. | 51/410 |
| 4,820,152 | 4/1989 | Warrin et al. | 433/219 |
| 4,893,440 | 1/1990 | Gallant et al. | 51/436 |
| 4,917,708 | 4/1990 | Yamaguchi et al. | 51/419 |
| 4,950,160 | 8/1990 | Karst | 433/88 |
| 5,035,750 | 7/1991 | Tada et al. | 134/437 |
| 5,066,335 | 11/1991 | Lane et al. | 134/51 |
| 5,145,717 | 9/1992 | Drury | 427/96 |
| 5,160,547 | 11/1992 | Kirschner et al. | 134/7 |
| 5,199,229 | 4/1993 | Herold et al. | 51/433 |
| 5,203,698 | 4/1993 | Blake et al. | 433/216 X |
| 5,256,703 | 10/1993 | Hermann | 521/120 |
| 5,275,561 | 1/1994 | Goldsmith | 433/216 |
| 5,312,251 | 5/1994 | Jackson | 433/88 |
| 5,330,354 | 7/1994 | Gallant | 433/88 |
| 5,334,016 | 8/1994 | Goldsmith et al. | 433/88 X |

*Primary Examiner*—Nicholas D. Lucchesi
*Attorney, Agent, or Firm*—John J. Connors; Connors & Associates

[57] ABSTRACT

A dental repair process removes an area of tooth decay from a tooth structure, and prepares the tooth structure, including dentin and enamel surfaces of the tooth structure, for bonding with a filler material. It is characterized by the use of a soft abrasive particulate material such as a urea resin with a Mohs hardness in the range of from 3.0 to 4.0 and a particle size of 10 to 200 microns. Such material is capable of effectively removing soft tooth decay when carried in a fluid stream that is directed towards the decayed area under pressure.

12 Claims, No Drawings

PROCESS FOR THE REMOVAL OF SOFT TOOTH DECAY USING A UNIQUE ABRASIVE FLUID STREAM

BACKGROUND OF THE INVENTION

1. Field of the Invention

This invention relates to employing a soft particulate abrasive in a fluid stream for removing soft tooth decay from a tooth.

2. Background Discussion

Using abrasives carried in a fluid stream to remove material in a precise manner is not new. Kirschner U.S. Pat. No. 5,160,547 discloses an air abrasion process for removing material from sensitive substrates in general, using sodium bicarbonate as the abrasive media. Carr U.S. Pat. No. 4,731,125 discloses an air abrasion method for cleaning paint from composite airplane panels using a plastic abrasive media. Drury U.S. Pat. No. 5,145,717 discloses an air abrasion method of resist removal in the manufacture of printed circuit boards using a plastic abrasive media.

Air abrasion in dentistry also is not new. Rzewinski U.S. Pat. No. 4,494,932 discloses an air abrasion apparatus and method for cleaning teeth, i.e., removing difficult stains and heavy plaque using an unspecified soluble powder. Karst U.S. Pat. No. 4,950,160 discloses an air abrasion instrument for polishing teeth using an unspecified abrasive powder. Finally, Goldsmith U.S. Pat. No. 5,275,561 discloses a fluid abrasion method of preparing a tooth structure, including dentin and enamel surfaces, for bonding a composite to the prepared surfaces using aluminum oxide as the abrasive material. While aluminum oxide works well as an abrasive for removal of hard caries material and on healthy tooth structure to roughen it as a pretreatment for bonding, it is inefficient in removing soft caries material from decayed tooth structure. The process of this invention provides a way to remove the soft caries material using an abrasive that is softer than aluminum oxide.

SUMMARY OF THE INVENTION

It is the primary objective of this invention to provide a more effective process for the removal of soft tooth decay using a relatively soft particulate material carried in a gaseous fluid stream directed at the decayed area.

The process of this invention has several features, no single one of which is solely responsible for its desirable attributes. Without limiting the scope of this invention as expressed by the claims which follow, its more prominent features will now be discussed briefly. After considering this discussion, and particularly after reading the section entitled, "DETAILED DESCRIPTION OF THE PREFERRED EMBODIMENT," one will understand how the features of this invention provide its advantages, which include simplified dental procedures for removing both hard and soft caries material and preparing tooth structure for filling with a restorative material.

The first feature of the dental repair process of this invention is that it is especially suited to remove soft tooth decay from a tooth. First, an abrasive fluid stream is created by metering an abrasive particulate material into a flowing gaseous fluid. The abrasive material is preferably a non-toxic polymeric composition having a hardness as measured on the Mohs scale in the range of from about 3.0 to about 4.0. The conventional abrasive particulate material has a hardness of about 9 on the Mohs scale. In accordance with this invention the abrasive material is a non-toxic thermoset plastic, for example, a urea resin. The average particle size of the abrasive material is from about 10 to about 200 microns. Abrasive particulates having a surface with jagged and sharp protuberances are excellent, but not required, for the purposes of this invention. Second, the fluid stream is directed towards the soft tooth decay for a time sufficient to break down the soft tooth decay into fragments which are carried away from the tooth by the fluid stream. It is believed that most of the abrasive particles shatter on contacting the surface of the tooth.

The removal of the tooth decay creates a cavity ready for filling with a restorative material, which may be either bonded or unbonded to the tooth. The restorative material may be a composite, amalgam, a metal, metallic alloy, porcelain, fused aluminum oxide, gold, titanium, or combinations of these restorative materials. The abrasive particulate material is variably metered at a rate between one gram per minute and fifteen grams per minute.

The second feature is that the abrasive fluid stream is carefully controlled. It may be directed towards the tooth structure as a continuous stream or in a series of pulses. The pulses are of short duration not exceeding about 2 seconds, with an interval between pulses not exceeding about 1 second. The fluid stream has a cross-sectional area in the range of from about 0.001 to about 0.0001 square inches, and its pressure ranges between about 10 to about 160 pounds per square inch gauge (psig). This fluid stream may be delivered with a surrounding stream of liquid such as water.

The third feature is that this process may be used to prepare a tooth for treatment with composites. Preferably, a bonding agent is applied to any exposed dentin surface area and nearby enamel surface area and then the composite material is applied over the bonding agent. The tooth decay is removed by directing the fluid stream through a nozzle normal (at a right angle) to the tooth decay and within about $\frac{1}{160}$ inch of the decay to make small cuts in the tooth decay. With the nozzle at an angle of from about 45° to about 90° and greater than $\frac{1}{16}$ inch away from the tooth decay, larger areas with straight walls are cut into the tooth decay. To prepare the underlying dentin surface area where the tooth decay was removed for bonding, the fluid stream is directed towards the tooth structure through a nozzle at an angle of less than about 45° held away from the underlying area a distance greater than about ¼ inch. This etches a broad section of the underlying area. This etching is performed immediately after decay removal, without any intervening processes which act directly to change the character of the tooth structure.

DESCRIPTION OF PREFERRED EMBODIMENT

Suitable equipment to remove soft decay with the urea resin material is made by Crystal Mark, Inc. of Glendale Calif. The resin material is generally available from many suppliers, for example, Maxi-Blast, Inc., South Bend, Ind. The recommended particle size is 150 U.S. standard sieve. This is equivalent to a particle size of about 100 microns. The range of particle sizes from about 100–200 U.S. standard sieve is suitable. If the material is purchased in a larger particle size, which is more readily available, it can be ground up to the recommended size. The recommended delivery rate of the resin is 5 grams per minute, though a range of 1–10 grams per minute may be suitable. The recommended fluid stream pressure is 60–70 psig. Air is most desirable as the carrier for the particles of abrasives, because of its ease of acquisition and safety. Other liquids or gases may also used, for example, nitrogen. For example, delivery of the abrasive laden fluid stream with a surrounding stream of water may enhance the comfort of the patient.

The removal of soft decay from a tooth is accomplished by the cutting action produced by impinging sharp-edged powder particles into the tooth's surface. A cylindrical shaped powder/air stream emerges from the nozzle and then diverges into a cone shape. With a close nozzle tip distance (less than approximately 1/160 inch), small holes and cuts with straight walls are made. To obtain sharp definition the nozzle tip distance should be kept to a minimum 1/32 inch. As the nozzle moves away from the tooth's surface, the hole diameter or width of cut increases, with the walls becoming angular. With a large nozzle tip distance, one wall can be kept normal to the surface by holding or setting the nozzle at an angle. The angle can be determined with a few trials. The cutting rate may be varied by adjusting the powder flow and using special type nozzles. Depressing a trigger on the hand piece, or depressing a foot pedal, causes the mixture of abrasive and air to be discharged from the nozzle. The amount of abrasive particulates is controlled by a powder flow controller which adjusts a powder vibrator voltage. Fluid pressure settings also vary the results. The time sufficient to remove the decay of course depends upon the volume of decay to be removed, but is usually about 5 to 30 seconds per tooth.

The roughening of the tooth structure for bonding is accomplished by etching a broad area. Simply increasing the nozzle tip distance and diverting the stream at an acute angle produces the desired roughening of the tooth surface. The time sufficient to prepare the surfaces for bonding of course depends upon the area of the surfaces to be prepared, but is usually about 15 to 45 seconds per tooth.

Additional steps to complete repair include application of the boding agent to the prepared area of the tooth structure, and application of a composite filling material. The typical composite material is selected from the group of: veneers, resins, glass ionomers, ceramics, porcelain and similar materials.

SCOPE OF THE INVENTION

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiment disclosed. On the contrary, the intention is to cover all modifications and alternate constructions coming within the spirit and scope of the invention as generally expressed by the following claims, which particularly point out and distinctly claim the subject matter of the invention.

We claim:

1. A dental repair process for removing soft tooth decay from a tooth, including
   (a) creating an abrasive fluid stream by metering abrasive particulates into a flowing fluid, said abrasive particulates being a non-toxic material having a hardness as measured on the Mohs scale in the range of between 3.0 and 4.0, and an average particle size of from 10 to 200 microns; and
   (b) directing said fluid stream towards the soft tooth decay for a time sufficient so that the fluid stream breaks down the soft tooth decay into fragments which are carried away from the tooth by the fluid stream.

2. The dental repair process of claim 1 where removal of the tooth decay creates a cavity ready for filling with a restorative material, said restorative material being either bonded or unbonded to the tooth.

3. The dental repair process of claim 2 where the restorative material is a composite, amalgam, a metal or metallic alloy, porcelain, fused aluminum oxide, gold, titanium, or combinations of these restorative materials.

4. The dental repair process of claim 1 where the abrasive particulates are variably metered at a rate between one gram per minute and fifteen grams per minute.

5. The dental repair process of claim 1 in which the abrasive particulates are formed of a non-toxic thermoset plastic.

6. The dental repair process of claim 5 in which the thermoset plastic is a urea resin.

7. The dental repair process of claim 1 where the abrasive fluid stream is directed towards the tooth as a continuous stream.

8. The dental repair process of claim 1 where the abrasive fluid stream is directed towards the tooth in a series of pulses of short duration not exceeding 2 seconds, with an interval between pulses not exceeding 1 second.

9. The dental repair process of claim 1 where the abrasive fluid stream has a cross-sectional area in the range of from 0.001 to 0.0001 square inches.

10. The process of claim 1 in which said fluid stream is delivered with a surrounding stream of liquid.

11. The process of claim 10 in which the liquid is water.

12. The process of claim 1 where the particles each have a surface with jagged and sharp protuberances.

\* \* \* \* \*